(12) United States Patent
Malandain

(10) Patent No.: US 8,641,769 B2
(45) Date of Patent: Feb. 4, 2014

(54) PLASTICALLY DEFORMABLE INTER-OSSEOUS DEVICE

(75) Inventor: Hugues Malandain, Shelton, CT (US)

(73) Assignee: Spine Wave, Inc., Shelton, CT (US)

( * ) Notice: Subject to any disclaimer, the term of this patent is extended or adjusted under 35 U.S.C. 154(b) by 0 days.

(21) Appl. No.: 13/809,329

(22) PCT Filed: Jun. 27, 2011

(86) PCT No.: PCT/US2011/042056
§ 371 (c)(1),
(2), (4) Date: Jan. 9, 2013

(87) PCT Pub. No.: WO2012/009152
PCT Pub. Date: Jan. 19, 2012

(65) Prior Publication Data
US 2013/0123927 A1 May 16, 2013

Related U.S. Application Data

(60) Provisional application No. 61/364,521, filed on Jul. 15, 2010.

(51) Int. Cl.
*A61F 2/44* (2006.01)
(52) U.S. Cl.
USPC .................................................. 623/17.16
(58) Field of Classification Search
USPC ................................ 623/17.11–17.16, 16.11
See application file for complete search history.

(56) References Cited

U.S. PATENT DOCUMENTS

| | | | |
|---|---|---|---|
| 4,932,975 A | 6/1990 | Main et al. | |
| 5,123,926 A | 6/1992 | Pisharodi | |
| 5,171,278 A | 12/1992 | Pisharodi | |
| 5,390,683 A | 2/1995 | Pisharodi | |
| 5,496,365 A | 3/1996 | Sgro | |
| 5,549,679 A | 8/1996 | Kuslich | |

(Continued)

FOREIGN PATENT DOCUMENTS

| | | |
|---|---|---|
| WO | 2009064787 A2 | 5/2009 |
| WO | 2009124269 A1 | 10/2009 |
| WO | 2010078468 A2 | 7/2010 |
| WO | 2010103344 A1 | 9/2010 |

OTHER PUBLICATIONS

Supplementary European Search Report for European Patent No. 11807269.3, dated Dec. 6, 2013, pp. 1-10.

*Primary Examiner* — Ellen C Hammond
*Assistant Examiner* — Jacqueline Johanas
(74) *Attorney, Agent, or Firm* — Hoffmann & Baron, LLP

(57) ABSTRACT

Described here are deformable, monolithic, stabilization devices, or implants, suitable for use within bone and between bones, for instance, to fuse vertebral bodies, to repair herniated discs, or to repair spinal compression fractures. The implants are introduced into a chosen site at a first, smaller height and then plastically deformed to achieve a second, but unique, pre-selected, larger height. Variations of the device provide one or more specific larger heights. The devices are particularly suitable as intervertebral spinal fusion implants for the immobilization of adjacent vertebral bodies. Methods of deploying the implants are also described as are instruments for such deployment.

Also described are variations of the device particularly suitable as sizing instruments. These versions are elastic, i.e., not plastically deformable, and may be restored to their original size. Many of the described variations include deformable regions serving as hinges. Other variations are non-monolithic or may have one or more classical hinges substituted for the deformable regions.

31 Claims, 16 Drawing Sheets

(56) References Cited

U.S. PATENT DOCUMENTS

| | | |
|---|---|---|
| 5,554,191 A | 9/1996 | Lahille et al. |
| 5,609,635 A | 3/1997 | Michelson |
| 5,665,122 A | 9/1997 | Kambin |
| 5,676,702 A | 10/1997 | Ratron |
| 5,693,100 A | 12/1997 | Pisharodi |
| 5,695,515 A | 12/1997 | Orejola |
| 5,782,832 A | 7/1998 | Larsen et al. |
| 5,800,549 A | 9/1998 | Bao et al. |
| 6,019,793 A | 2/2000 | Perren et al. |
| 6,039,761 A | 3/2000 | Li et al. |
| 6,126,689 A | 10/2000 | Brett |
| 6,143,031 A | 11/2000 | Knothe et al. |
| 6,159,244 A | 12/2000 | Suddaby |
| 6,174,334 B1 | 1/2001 | Suddaby |
| 6,183,517 B1 | 2/2001 | Suddaby |
| 6,193,757 B1 | 2/2001 | Foley et al. |
| 6,206,923 B1 | 3/2001 | Boyd et al. |
| 6,224,604 B1 | 5/2001 | Suddaby |
| 6,293,967 B1 | 9/2001 | Shanley |
| 6,332,895 B1 | 12/2001 | Suddaby |
| 6,395,031 B1 | 5/2002 | Foley et al. |
| 6,409,766 B1 | 6/2002 | Brett |
| 6,436,140 B1 | 8/2002 | Liu et al. |
| 6,443,989 B1 | 9/2002 | Jackson |
| 6,469,309 B1 | 10/2002 | Kasai |
| 6,488,710 B2 | 12/2002 | Besselink |
| 6,500,205 B1 | 12/2002 | Michelson |
| 6,544,265 B2 | 4/2003 | Lieberman |
| 6,551,319 B2 | 4/2003 | Lieberman |
| 6,582,431 B1 | 6/2003 | Ray |
| 6,582,451 B1 | 6/2003 | Marucci et al. |
| 6,723,126 B1 | 4/2004 | Berry |
| 6,743,255 B2 | 6/2004 | Ferree |
| 6,773,460 B2 | 8/2004 | Jackson |
| 6,808,537 B2 | 10/2004 | Michelson |
| 6,821,298 B1 | 11/2004 | Jackson |
| 6,833,006 B2 | 12/2004 | Foley et al. |
| 6,835,206 B2 | 12/2004 | Jackson |
| 6,893,464 B2 | 5/2005 | Kiester |
| 6,972,035 B2 | 12/2005 | Michelson |
| 7,018,415 B1 | 3/2006 | McKay |
| 7,022,138 B2 | 4/2006 | Mashburn |
| 7,097,648 B1 | 8/2006 | Globerman et al. |
| 7,118,579 B2 | 10/2006 | Michelson |
| 7,122,043 B2 | 10/2006 | Greenhalgh et al. |
| 7,122,052 B2 | 10/2006 | Greenhalgh |
| 7,128,760 B2 | 10/2006 | Michelson |
| 7,179,024 B2 | 2/2007 | Greenhalgh |
| 7,396,365 B2 | 7/2008 | Michelson |
| 7,625,377 B2 | 12/2009 | Veldhuizen et al. |
| 7,655,042 B2 | 2/2010 | Foley et al. |
| 7,670,375 B2 * | 3/2010 | Schaller ............ 623/17.11 |
| 7,678,148 B2 | 3/2010 | Peterman |
| 7,846,206 B2 | 12/2010 | Oglaza et al. |
| 7,993,403 B2 | 8/2011 | Foley et al. |
| 8,133,232 B2 | 3/2012 | Levy et al. |
| 8,267,939 B2 * | 9/2012 | Cipoletti et al. ............ 606/99 |
| 8,382,842 B2 * | 2/2013 | Greenhalgh et al. ....... 623/17.16 |
| 8,430,930 B2 | 4/2013 | Hunt |
| 2002/0045945 A1 | 4/2002 | Liu et al. |
| 2003/0093154 A1 | 5/2003 | Estes et al. |
| 2004/0010315 A1 | 1/2004 | Song |
| 2004/0133280 A1 | 7/2004 | Trieu |
| 2005/0021041 A1 | 1/2005 | Michelson |
| 2005/0027359 A1 | 2/2005 | Mashburn |
| 2005/0080489 A1 | 4/2005 | Estes et al. |
| 2005/0159813 A1 | 7/2005 | Molz, IV |
| 2005/0192671 A1 | 9/2005 | Bao et al. |
| 2005/0216017 A1 | 9/2005 | Fielding et al. |
| 2005/0283245 A1 | 12/2005 | Gordon et al. |
| 2006/0004455 A1 | 1/2006 | Leonard et al. |
| 2006/0058807 A1 | 3/2006 | Landry et al. |
| 2006/0058880 A1 | 3/2006 | Wysocki et al. |
| 2006/0095136 A1 | 5/2006 | McLuen |
| 2006/0149385 A1 | 7/2006 | McKay |
| 2006/0224241 A1 | 10/2006 | Butler et al. |
| 2006/0241774 A1 | 10/2006 | Attali et al. |
| 2006/0253201 A1 | 11/2006 | McLuen |
| 2006/0287725 A1 | 12/2006 | Miller |
| 2007/0032791 A1 | 2/2007 | Greenhalgh |
| 2007/0032872 A1* | 2/2007 | Simonton et al. .......... 623/17.11 |
| 2007/0073398 A1 | 3/2007 | Fabian et al. |
| 2007/0093901 A1 | 4/2007 | Grotz et al. |
| 2007/0118222 A1 | 5/2007 | Lang |
| 2007/0219634 A1 | 9/2007 | Greenhalgh et al. |
| 2007/0225807 A1* | 9/2007 | Phan et al. ................. 623/17.11 |
| 2007/0233254 A1 | 10/2007 | Grotz et al. |
| 2007/0244485 A1 | 10/2007 | Greenhalgh et al. |
| 2007/0260260 A1 | 11/2007 | Hahn et al. |
| 2007/0282443 A1* | 12/2007 | Globerman et al. ....... 623/17.11 |
| 2008/0009866 A1 | 1/2008 | Alamin et al. |
| 2008/0058933 A1 | 3/2008 | Garner et al. |
| 2008/0071356 A1 | 3/2008 | Greenhalgh et al. |
| 2008/0097332 A1 | 4/2008 | Greenhalgh et al. |
| 2008/0108993 A1 | 5/2008 | Bennett et al. |
| 2008/0119886 A1 | 5/2008 | Greenhalgh et al. |
| 2008/0161825 A1 | 7/2008 | Greenhalgh et al. |
| 2008/0167657 A1 | 7/2008 | Greenhalgh |
| 2008/0183105 A1 | 7/2008 | Greenhalgh et al. |
| 2008/0183204 A1 | 7/2008 | Greenhalgh et al. |
| 2008/0281346 A1 | 11/2008 | Greenhalgh et al. |
| 2008/0281423 A1 | 11/2008 | Sheffer et al. |
| 2008/0294205 A1 | 11/2008 | Greenhalgh et al. |
| 2008/0319549 A1 | 12/2008 | Greenhalgh et al. |
| 2009/0018524 A1 | 1/2009 | Greenhalgh et al. |
| 2009/0024204 A1 | 1/2009 | Greenhalgh et al. |
| 2009/0105757 A1 | 4/2009 | Gimbel et al. |
| 2009/0222100 A1 | 9/2009 | Cipoletti et al. |
| 2009/0240335 A1* | 9/2009 | Arcenio et al. ............ 623/17.16 |
| 2009/0276048 A1* | 11/2009 | Chirico et al. ............. 623/17.11 |
| 2010/0082109 A1 | 4/2010 | Greenhalgh et al. |
| 2010/0121453 A1 | 5/2010 | Peterman |
| 2010/0174375 A1* | 7/2010 | Schaller .................... 623/17.16 |
| 2010/0185291 A1* | 7/2010 | Jimenez et al. ............ 623/17.16 |
| 2010/0292796 A1* | 11/2010 | Greenhalgh et al. ....... 623/17.11 |
| 2011/0046739 A1 | 2/2011 | Oglaza et al. |
| 2011/0137421 A1* | 6/2011 | Hansell et al. ............. 623/17.16 |
| 2012/0071977 A1* | 3/2012 | Oglaza et al. ............. 623/17.11 |
| 2012/0245691 A1* | 9/2012 | Reimels .................... 623/17.16 |

* cited by examiner

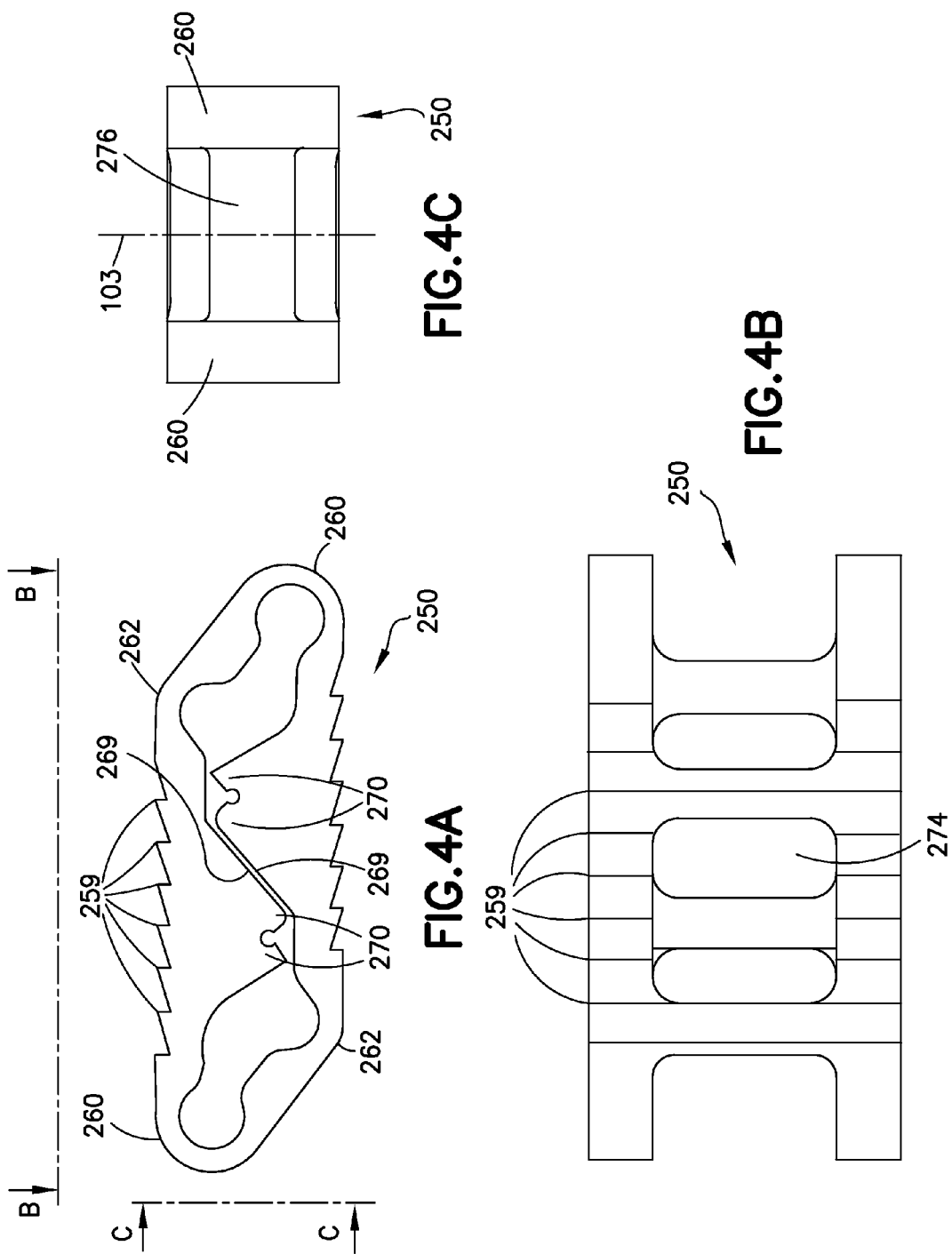

PLASTICALLY DEFORMABLE INTER-OSSEOUS DEVICE

FIELD

Described here are deformable, monolithic, stabilization devices, or implants, suitable for use within bone and between bones, for instance, to fuse vertebral bodies, to repair herniated discs, or to repair spinal compression fractures. The implants are introduced into a chosen site at a first, smaller height and then plastically deformed to achieve a second, but unique, pre-selected, larger height. Variations of the device provide one or more specific larger heights. The devices are particularly suitable as intervertebral spinal fusion implants for the immobilization of adjacent vertebral bodies. Methods of deploying the implants are also described as are instruments for such deployment.

Also described are variations of the device particularly suitable as sizing instruments. These versions are elastic, i.e., not plastically deformable, and may be restored to their original size. Many of the described variations include deformable regions serving as hinges. Other variations are non-monolithic or may have one or more classical hinges substituted for the deformable regions.

BACKGROUND

Some conditions of the spine result from degradation or injury to the bone structures, e.g., the vertebral bodies, of the spine. These conditions may be the result of bone degeneration such as by osteoporosis or trauma, or by injuries such as compression fractures. Any of these maladies can cause great pain.

Other ailments of the spine result in degeneration of the spinal disc in the intervertebral space between the vertebral bodies. These include degenerative disc disease and traumatic injuries. In any case, disc degeneration can cause pain and other complications. That deformation is commonly known as a herniated or "slipped" disc. The protrusion may press upon one or more of the spinal nerves exiting the vertebral canal through the partially obstructed foramen, causing pain or paralysis in the area of the spinal nerve's influence. Conservative treatment can include non-operative treatment requiring patients to adjust their lifestyles and submit to pain relievers and a level of underlying pain. Operative treatment options include disc removal. This can relieve pain in the short term, but also often increases the risk of long-term problems and can result in motor and sensory deficiencies resulting from the surgery. Disc removal and more generally disc degeneration disease are likely to lead to a need for surgical treatment in subsequent years. The fusion or fixation will minimize or substantially eliminate relative motion between the fixed or fused vertebrae. In surgical treatments, adjacent vertebra may be fixated or fused to each other using devices or bone grafts. These may include, for example, screw and rod systems, interbody spacers, threaded fusion cages and the like.

Some fixation or fusion devices are attached to the vertebra from the posterior side. Such devices protrude from the back and require hardware for separate attachment to each vertebra. Fusion cages and allografts are contained within the intervertebral space, but must be inserted into the intervertebral space in the same dimensions as desired to occupy the intervertebral space. This requires that an opening sufficient to allow the cage or graft must be created through surrounding tissue to permit the cage or graft to be inserted into the intervertebral space.

The described implants are suitable for fusing adjacent vertebrae where at least a portion of the natural disc between those vertebrae has been removed but are introduced into the volume at a small profile that is expanded to a larger profile after placement.

Human vertebral bodies have a hard outer shell of compacted, dense cortical bone (sometimes referred to as the "cortex") and a relatively softer, inner mass of cancellous bone. Just below the cortex adjacent the disc is a region of bone referred to as the "subchondral zone." The outer shell of compact bone (the bony endplate) adjacent to the spinal disc and the underlying subchondral zone are often referred to as the bony "end plate region." The endplate region is the densest bone available to support a fusion implant. Removal of, or compromise of, the endplate region by preparing the bone surface, e.g., by cutting into or boring into the cortex, allows implants to contact the softer and less dense cancellous bone that lies beneath the endplate. It is desirable to maintain the integrity of the cortex, if possible, in implanting fusion devices.

Complicating this desire to maintain the integrity of the vertebral bone surface adjacent the disc is the fact that that surface is somewhat dome-shaped. Such a dome-shaped surface does not always provide a predictable surface upon which to situate a fusion device. Additionally, many maladies related to discs cause the situations requiring distraction of the discs as part of the treatment. This means that the space between vertebrae is small.

There are a variety of implants for spinal fusion in current use.

One such implant has a modified cylindrical or tapered cylindrical shape. Implantation of such an implant requires a drilling step to create an adequate opening into the intervertebral space and a bore across the faces of the endplates. Since the surfaces of the upper and lower vertebral bodies adjacent the disc space are dome-shaped, some additional consideration must be given to gaining adequate contact between the vertebral bodies and the implant to achieve fusion.

One solution is shown in U.S. Publ. Appl. No. 2006/0241774, to Attali et al, in which a cylindrical plug is inserted into a bore in the intervertebral space and then expanded.

Non-cylindrical implants that are pushed into the disc space after a discectonmy are also known. Although these push-in implants do have the advantage of supporting the adjacent vertebral bodies by contacting a substantial portion of the vertebral endplates, they do not offer the advantages associated with threaded cylindrical implants that are screwed into a bore in the adjacent vertebral bodies to more securely hold these implants in their final fully seated positions. Further, unless the endplate is at least partially decorticated, i.e. worked upon to access the vascularity deep to the outer most aspect of the endplate itself, fusion will not occur.

The implants are suitable as actors in vertebroplasty. Vertebroplasty is an image-guided, minimally invasive, nonsurgical, distractive, therapy used to strengthen broken vertebrae, whether the vertebrae are weakened by disease, such as osteoporosis or cancer, or fractured by stress.

Spinal fusion and vertebroplasty procedures often include a step of injecting an orthopedic cement mixture into the intervertebral space or into the fractured bone. The cement mixture may contain particulate osteogenic materials, e.g., mixtures of one or several calcium phosphate powders that react with water to form other calcium phosphate compounds, often an apatite, or others listed below. These cement mixtures are quite viscous and are difficult to inject through small diameter openings. Providing large passageways through the implant allows passage of the cement through the implant.

None of the cited documents disclose the described deformable implant.

BRIEF DESCRIPTION OF THE DRAWINGS

FIGS. 4A, 4B, and 4C show, respectively, side, top, and end views of the variation of the implant shown in FIGS. 3A and 3B.

DESCRIPTION

Described herein is a bone stabilization device that may be used in an interosseous space, i.e., inside a bone or between bones, where the space is defined generally as being directly or indirectly between bony surfaces, in particular, the described device is suitable as an intervertebral spinal fusion implant that is introduced at a low profile and expanded to a high profile at the implantation site. The implant may be monolithic and expanded by deformation of the monolithic body. In many variations, the implant may be expanded to a unique preselected height. Other variations of the implant may be expanded to a specific, discrete height selected from two or more unique preselected heights. Expansion of the implant from the low profile rotates components of one or more, partial, load-bearing, integral, support columns into alignment upon reaching the final high profile. The expansion takes place in a single plane or single direction. The components of the support columns may latch to each other or otherwise interact or engage with each other to limit the expansion to the specific, discrete, predetermined heights or to lock the implant into the expanded configuration while providing high compressive strength to the implant.

Described here are monolithic implants that are expanded from a lower height to a higher one by permanent, plastic deformation of the implant in a particular plane. The implant incorporates partial support components that become aligned during the process of deformation (and expansion) and cooperate to form a complete support component that typically supports a major portion of stress applied to the implant. In some variations of the implant, there may be a small gap between the partial support components after expansion; the small gap may disappear upon compression during use.

Figure 1A:
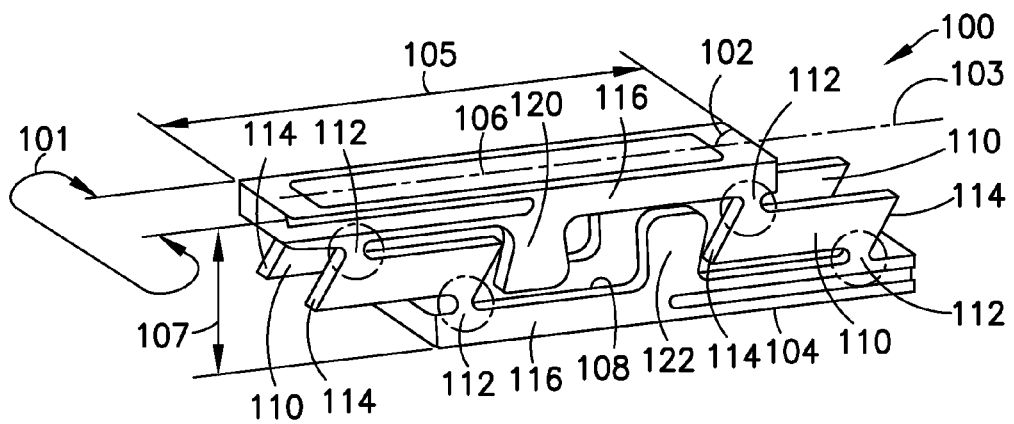
FIGS. 1A-1C show perspective views of one variation of the implant, respectively, in collapsed form, partially expanded form, and fully expanded form.
Figure 1B:
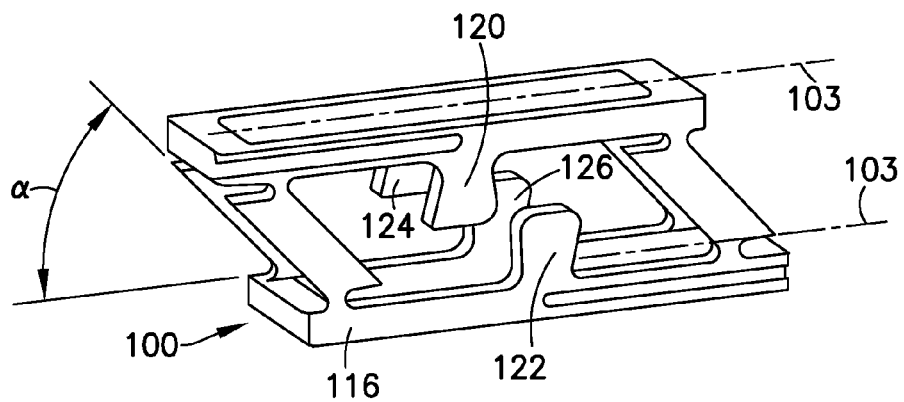
Figure 1C:
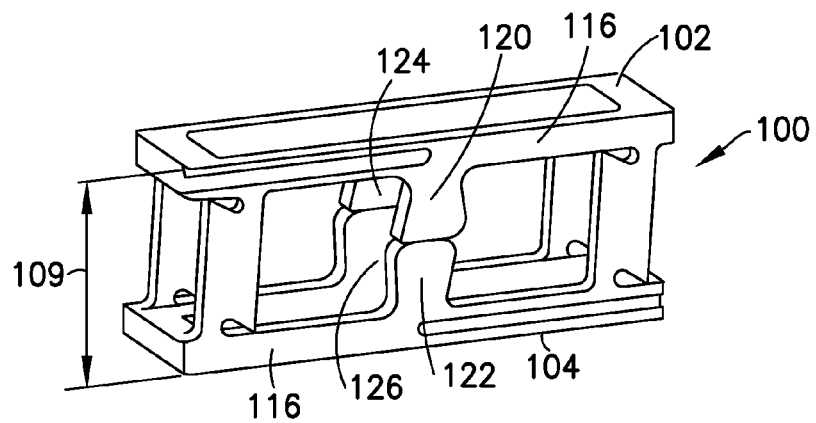

FIGS. 1A-1C show a variation of the implant showing the generalized expansion by deformation and providing a set of common terms for components of the implant and its geometry.

FIG. 1A shows the implant (100) in its lower profile configuration as might be utilized during initial introduction of the implant into a treatment site. FIG. 1B shows the implant (100) during the course of expansion. FIG. 1C shows the implant (100) after complete expansion and permanent deformation of the device.

Returning to FIG. 1A, the implant (100) includes an upper bone contact surface (102) and a lower bone contact surface (104) that, when the implant (100) is expanded, generally contact adjacent bone surfaces, e.g., vertebral bone surfaces facing or defining a volume between vertebrae in a spine from which a natural disc has been removed in preparation for the implantation of the device. As will be discussed below, the implant has a variety of uses other than as a spinal stabilizer or fusion block.

Often, bone contact surfaces (102, 104) will include fixation components of some design, e.g., spikes, serrations, fins, etc., as will be described below. These fixation components have the goal of limiting movement of the implant along (or parallel to) the bone surface and, in some instances, provide for permanent ingrowth between bone and implant.

The upper and lower bone contact surfaces (102, 104) each have a width (101), generally perpendicular to the longitudinal axis (103) of the implant (100) and a length (105) along and generally parallel to the axis (103) of the implant (100). The collapsed height (107) of this variation of the implant (100) is the distance between the upper and lower bone contact surfaces (102, 104) prior to expansion.

The upper and lower bone contact surfaces (102, 104) may include openings (106, 108) allowing osteogenic materials to flow into the center volume of the implant and to pass through that volume to adjacent bone surfaces thereby aiding in fusion of the implant to and between adjacent bony surfaces.

In any event, the device comprises a plurality of rotating or locator arms (110) that rotate around deformation joint areas (112). This locator arm (110) design includes lands (114) at each end of the locator arms (110) that contact surfaces on the bone contact surface structure (116). Rotation of the locator arms (110) and the resultant deformation of the deformation joint areas (112), causes expansion of the implant (100) to the expanded height (109) shown in FIG. 1C.

Central to this variation of the device are the deformation joint areas (112). Those joints (112) are regions or areas of the device located between substantially inflexible regions or structures of the device. The joints have two functions: 1.) each provides a center of rotation or locus of bending between the adjacent inflexible regions—a hinging effect—, and 2.) each provides a region in which, after expansion, all of the deformation in the device is located.

The deformation joints (112) shown in FIGS. 1A-1C may be operative to provide a sharp bend, as may be seen in FIGS. 1A-1C, in which the deformation is located in a comparatively smaller area or may be operative to provide a longer bend in which the deformation is located in a comparatively larger area.

The deformation joints (112) may be formed by providing a reduced cross-sectional area of a structural component. The reduced cross-section provides a region of reduced strength and localized bending and, in properly chosen materials, plastic deformation.

In the variation shown in FIGS. 1A-1C, the deformation joint areas (112) permit bending and deformation between the substantially inflexible locator arms (110) and the substantially inflexible upper or lower bone contact surface structures (116). Although I use the term "substantially inflexible" with respect to the locator arms and columns, those component structures will have some amount of flexibility due to the size and materials of manufacture of the components. In general, the locator arms and columns are less flexible, typically significantly less flexible, than the deformation joint areas.

FIG. 1B shows the implant (100) after it has been partially deformed at an angle (α). The implant is expanded by providing differential, relative movement between upper bone contact surface (102) and the lower bone contact surface (104). That differential movement expands the device in only a single direction, the height.

As the device (100) is deformed and expanded through the sequence shown in FIGS. 1A-1C, cooperating partial load-bearing columns, an upper partial column (120) and a lower partial column (122), move into alignment and engage to form a complete column as the expansion is complete. The term "engage" is meant herein to encompass situations in which the two partial load-bearing columns (120, 122) are in contact and in which the two partial load-bearing columns (120, 122) include a small gap between them after expansion, provided that the gap disappears under load during use.

S shown in FIG. 1C, the partial load-bearing columns (120, 122 and 124, 126), after expansion, provide the major load-bearing component for loads imposed upon the upper and lower bone contact surfaces (102, 104). A pair of partial load-bearing columns (124, 126) is situated on the opposite side of the device (100).

The variation of an implant shown in FIGS. 1A-1C includes upper and lower bone contact surfaces (102, 104) that are substantially parallel. As discussed below, these surfaces need not be parallel. For instance, when the implant is used to replace a lumbar disc, the implant may be designed in such a way that the bone contact surfaces are not parallel to provide a lordotic angle after implantation. This concept will be discussed further below.

The upper and lower bone contact surfaces (102, 104) are shown to be substantially flat, but may have shapes or forms, e.g., partially cylindrical, rounded, elliptical, spherical, etc. Such shapes may be chosen, e.g., to perform or provide a specific function or to match an anatomical shape.

Figure 2A:
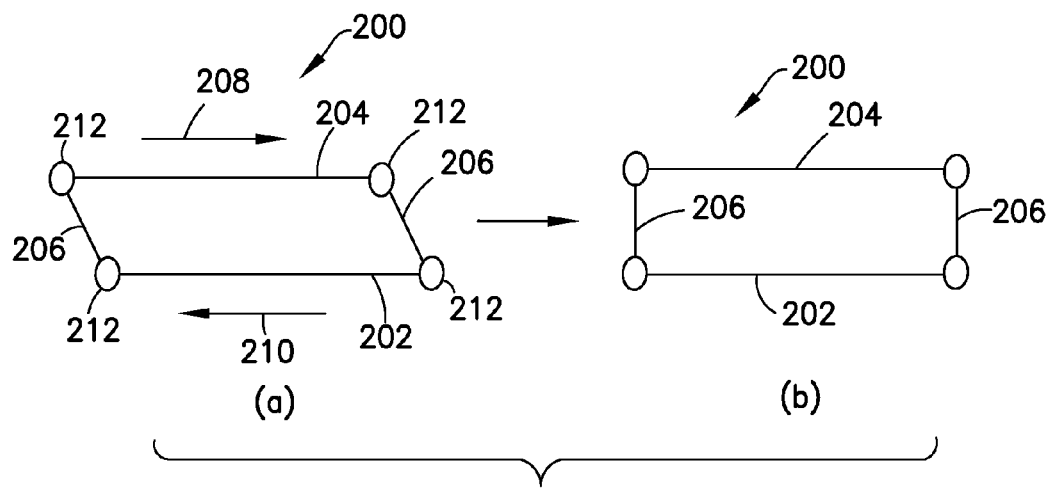
FIGS. 2A and 2B are schematic drawings showing operation of some variations of the implant.
Figure 2B:
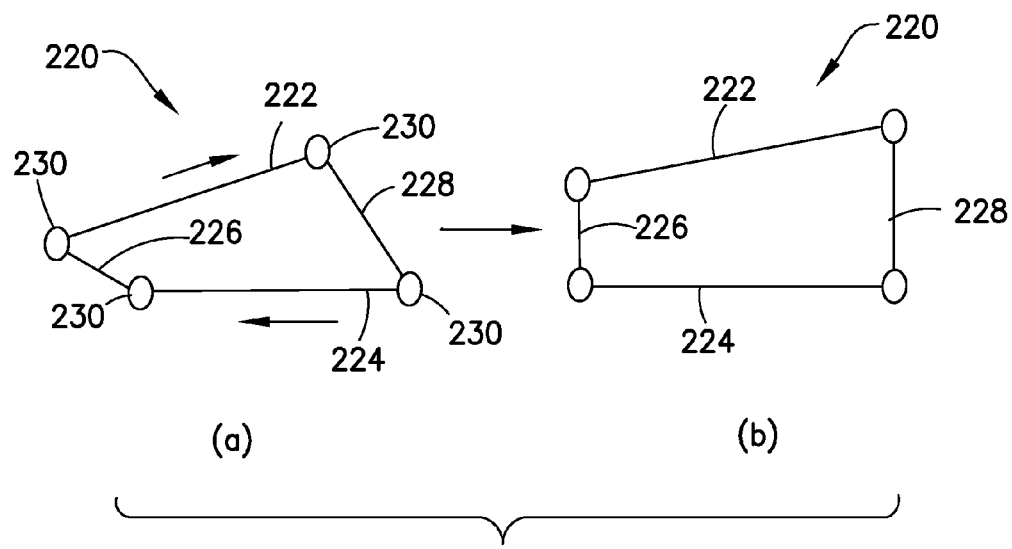

FIGS. 2A and 2B show, in schematic fashion, an explanation of one aspect of the operation of the implant, and explaining in particular, the geometry of the generally inflexible members discussed above, both when the device is collapsed (as at implantation) and when it is expanded.

FIG. 2A shows a variation of the implant similar to those shown in FIGS. 1A-1C and 3A-3B. In this variation, the device (200) has substantially parallel lower (202) and upper (204) bone contact surface structures. The locator arms (206) in this variation are also substantially parallel. Each of the upper and lower bone contact surfaces (202, 204) and the locator arms (206) are considered to be inflexible.

In step (a), the device (200) is depicted in a collapsed form. As the lower and upper bone contact surface structures (202, 204) are moved in the directions shown by arrows (208, 210), the inflexible rotator arms (206) rotate about their deformation joints (212) to result in the expanded condition shown in step (b).

FIG. 2B shows a device (220) in which neither pair of inflexible members, i.e., upper and lower bone contact surface structures (222, 224) or distal and proximal locator arms (226, 228), are parallel. As noted elsewhere, an expanded structure in which the bone contact surfaces (227, 224) are not parallel, may be useful in treating certain conditions or portions of the anatomy where the adjacent bone surfaces either are not generally parallel and should be or that are not parallel and should remain so.

Step (a) shows the device (220) in a collapsed form. As the upper and lower bone contact surface structures (222, 224) move in relative directions generally opposite each other (230, 232). The various inflexible members (222, 224, 226, 228) rotate about deformation joints (230) to result in the structure schematically depicted in step (b).

The final expanded shape of the implant (220) is fixed using components not shown in FIGS. 2A and 2B—the partial column supports discussed above and shown in FIGS. 1A-1C.

Figure 3A:
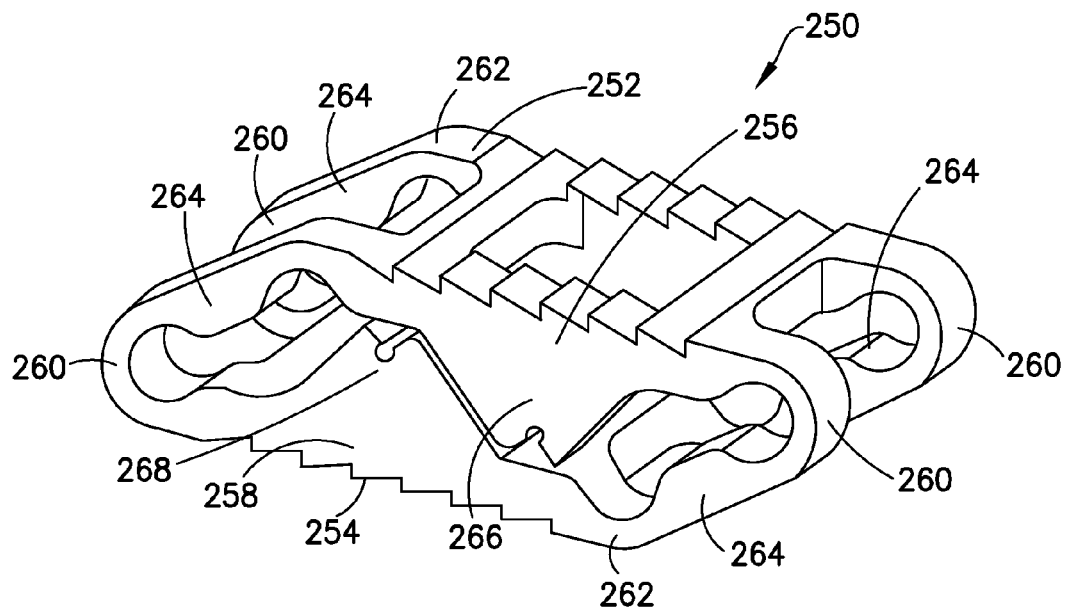
FIGS. 3A and 3B show perspective views of one variation of the implant, respectively, in collapsed form and fully expanded form.
Figure 3B:
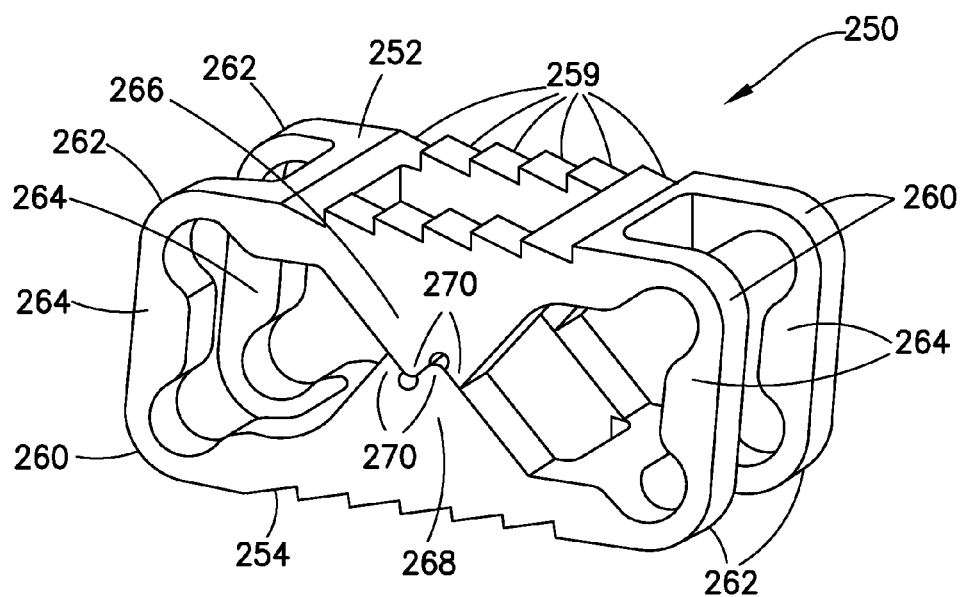

FIGS. 3A and 3B show perspective views of another variation of the device (250), respectively in collapsed form and in expanded form. FIGS. 4A, 4B, and 4C show side, top, and end views of that implant (250). These figures provide greater detail of certain ancillary features of the implant, e.g., components useful in expanding and implanting the device in cooperation with suitable instrumentation, bone anchoring features, and latch components operative as portions of the support columns.

The variation (250) depicted in FIGS. 3A, 3B, and 4A-4C includes bone contact surfaces (252, 254) that are parallel both in the compressed form and in the expanded form. As noted above, the geometry of the inflexible components of the implant need not involve parallel surfaces, but may be non-parallel if desired.

FIG. 3A shows an upper bone contact surface (252) defined by the underlying bone contact surface structure (256). A lower bone contact surface (254), not seen, is defined by the lower bone contact surface structure. The upper bone contact surface (252) includes a number of serrations (259) serving a bone anchoring function. These functional anchors may assist in holding a bone contact surface on the implant (250) in position during implantation or may hold the implant in position after implantation. Other forms of functional bone anchoring components, e.g., fins, spikes, hooks, etc., may be substituted as the designer desires.

Deformable joint regions—encompassing acute angles (260) and obtuse angles (262)—are seen at each corner of the device (250). These joint regions are physically defined by their actual deformation during expansion of the device (250) and ultimately after the device (250) is fully expanded. The inflexible regions between deformable joint regions (260, 262) are either bone-contact surface structures (256, 258) or locator arms (264).

This variation of the implant (250) includes upper and lower partial load-bearing columns (266, 268) that move into contact (as shown in FIG. 3B) as the implant is expanded and ultimately latch together by intermeshing a pair of teeth (270) at the apex of the upper and lower partial load-bearing columns (266, 268). After latching, the two partial load-bearing columns (266, 268) form a complete load-bearing column.

FIG. 4A shows a side view of the implant (250). The deformable joint regions (260, 262) include thinned areas accentuating the devices' tendency to deform only in those regions. As a practical matter, where the implant is monolithic, thinning a region of the implant to form deformation regions for the "hinging" effect is an excellent way to produce such regions. Other ways, e.g., localized annealing of the desired deformation regions, localized hardening of the non-deformation-regions, and providing a different, elastically composition in the deformation regions are also suitable but provided with less ease.

FIG. 4A shows another optional feature: the faces (269) or edges of the partial load-bearing columns (268) that are adjacent each other do not contact each other until the latching teeth (270) form the load-bearing column at expansion. Those surfaces (270) may, of course, be in contact.

FIG. 4B is a top view of the implant (250) showing the bone contact surface and its serrations (259). In particular, the drawing shows the large openings (274) allowing access from the interior of the implant (250), e.g., osteogenic materials, bone cement, granular bone, etc., may be introduced to the bone surfaces adjacent a properly positioned implant (258) through the center of the implant (250). Suitable osteogenic materials are discussed below. The sizes of the openings may be larger or smaller as desired or as dictated by the implant use.

FIG. 4C provides an end view of the implant (250). The acute-angle deformable joint region (260) may be seen. The figure also shows a longitudinal passageway (276) allowing passage of osteogenic filler material.

Figure 5:
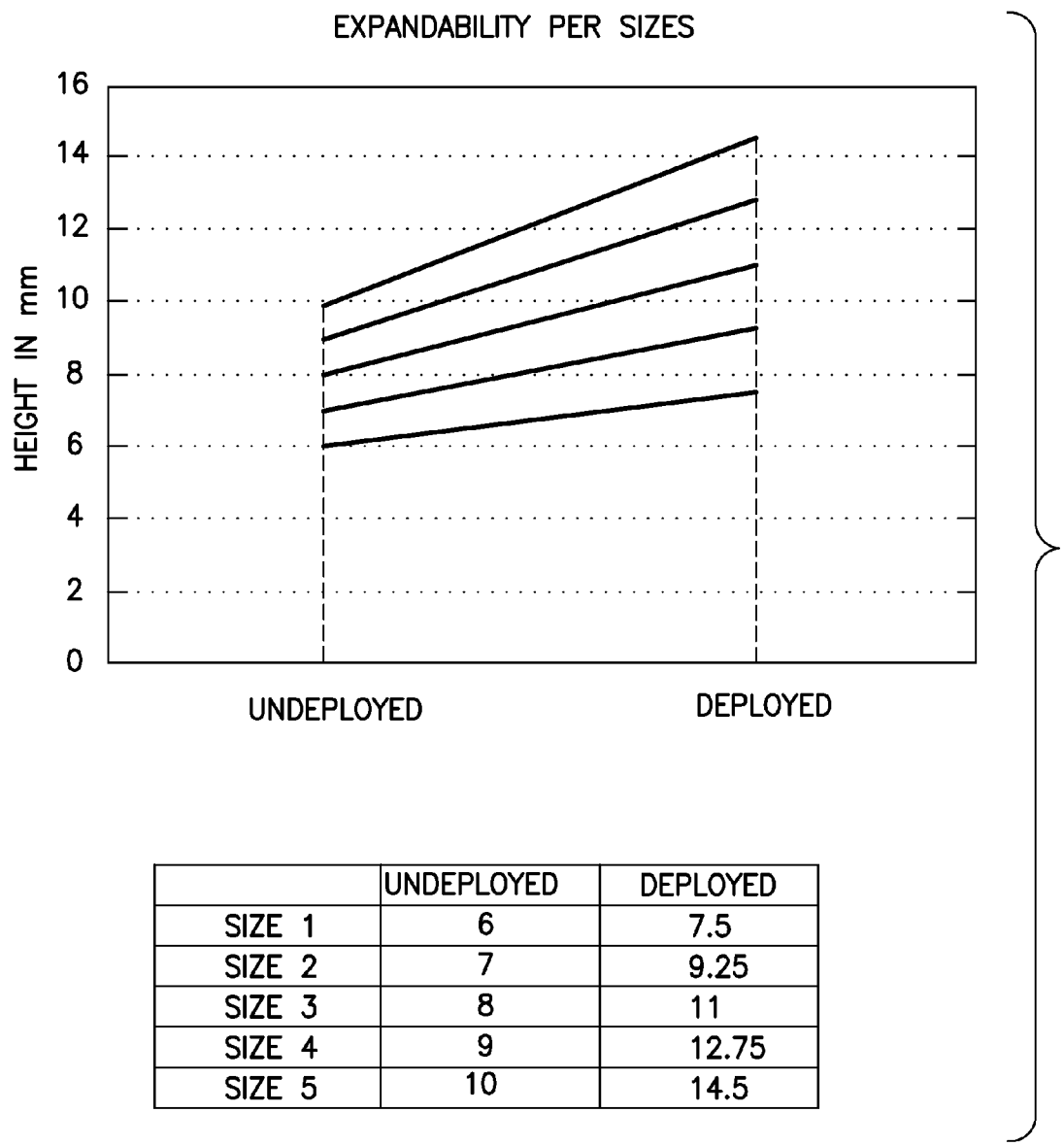
FIG. 5 is a graph and table showing potential expandability of a specific variation of the implant shown in FIGS. 3A and 3B.

FIG. 5 is a graph and table relating to the expandability of a number of examples of the implants of the design shown in FIGS. 3A, 3B, and 4A-4C. A small implant having a 6 mm collapsed height expands to 7.5 mm, a 25% increase in height. The larger implant having a 10 mm collapsed height expands to 14.5 mm, a 45% increase in height. Other sizes and expansion ratios may be designed. Expanded lengths of between 5 mm and 30 mm and expanded heights of about 2 mm and 15 mm are practical sizes and easily designed based upon the directions provided here. Similarly, expanded aspect ratio (length:height) between 0.5 and 4:1 are easily designed although I have found ratios in the range of 1.5:1.0 to 3:1.0 to be quite useful in implants for human spinal fusion service.

Figure 6A:
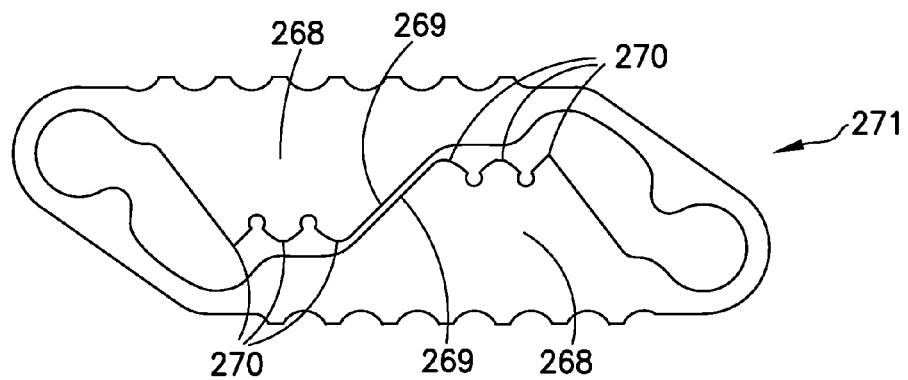
FIGS. 6A and 6B show side views of one variation of the implant, respectively, in collapsed form and fully expanded form.
Figure 6B:
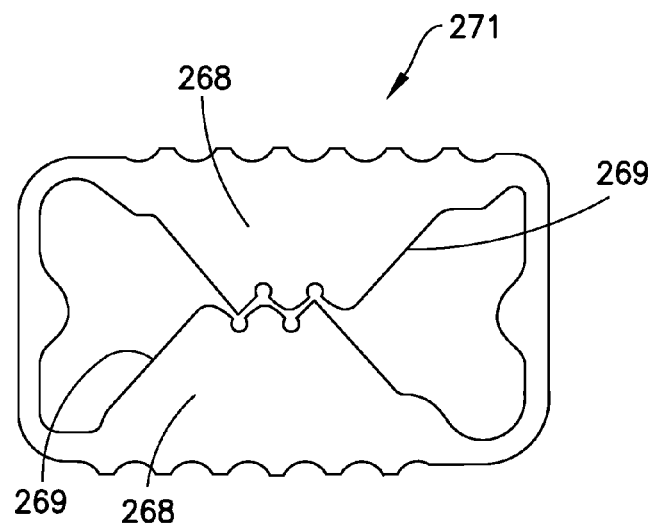

FIGS. 6A and 6B show perspective views of another variation of the device (271), respectively in collapsed form and in expanded form. This variation (271) is substantially similar to the variation shown in FIGS. 3A and 3B except that the implant comprises two sets of interlocking teeth (270).

Specifically, this variation of the implant (271) includes upper and lower partial load-bearing columns (266, 268) that move into contact (as shown in FIG. 6B) as the implant is expanded and ultimately latch together by intermeshing a two pairs of teeth (270) at the apex of the upper and lower partial load-bearing columns (266, 268). After latching, the two partial load-bearing columns (266, 268) form a complete load-bearing column.

Figure 7:
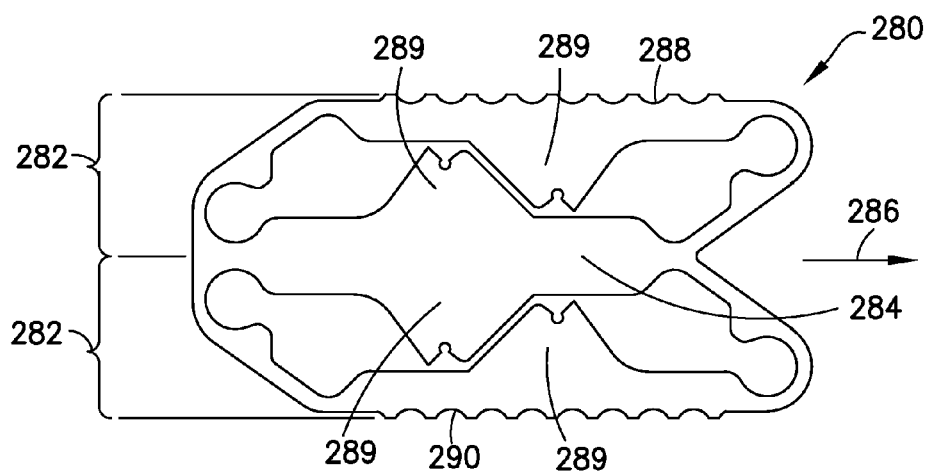
FIGS. 7 and 8 show side views of multi-cell versions of the described implant.
Figure 8:
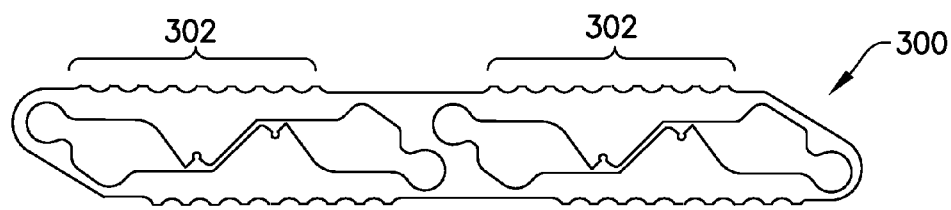

FIGS. 7 and 8 show implants that are, in essence, multi-cell variants of these shown in FIGS. 3A-4C.

FIG. 7 shows a multi-cell implant (280) having two stacked integral cells (282) in a single monolithic device. This variation is suitable for a vertebral body replacement ("VBR"), i.e., a replacement for a pair of discs and a vertebra in a spine. The multiple, but short, partial column supports (289) provide added stability to such a long device. The device (280) is shown in a collapsed condition. In this variation, expansion of the device (280) involves differential or relative movement of center section (284) in the direction of the arrow (286) with relation to the upper bone contact area (288) and the lower bone contact area (290).

FIG. 8 shows a multi-cell implant (300) having two integral cells (302) placed end-to-end in a single monolithic device. The device (300) is shown in a collapsed condition.

Figure 9:
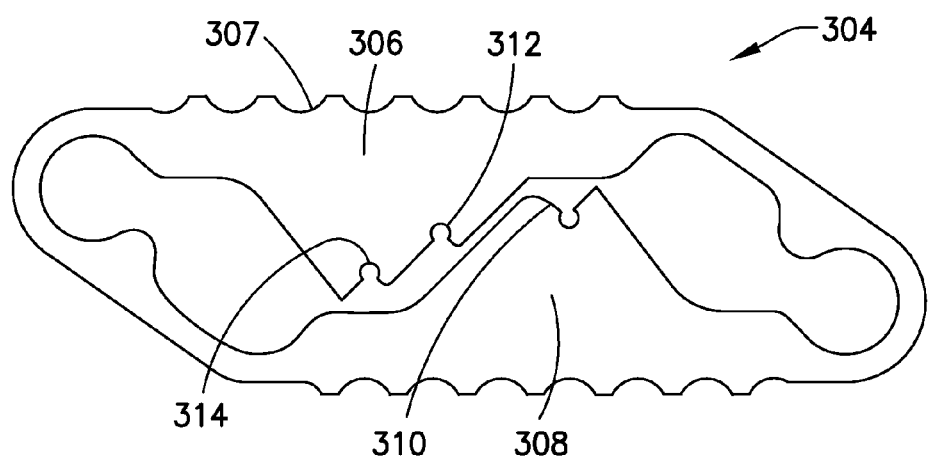
FIG. 9 shows a side view of a version of the implant having multiple expansion points.

FIG. 9 shows a variation of the implant (304) having multiple—in this instance, two—discrete, pre-determined expansion sizes. The overall design is similar to the design seen in FIG. 3A-4C. The device (304) has an upper partial load-bearing column (306) and a lower partial load-bearing column (308). The lower partial load-bearing column (308) includes a pair of teeth (310) at its apex forming a portion of an expansion latch. The upper partial load-bearing column (306) includes two latching sites—a lower height site (312) at an intermediate position on the upper partial load-bearing column (306) and a higher height site (314) at the apex of the upper partial load-bearing column (306). After latching the pair of teeth (310) situated on the lower partial load-bearing column (308) with one or the other of the lower height site (312) or the higher height site (314), the two partial load-bearing columns (306, 308) form a complete load-bearing column at one of the predetermined heights.

Figure 10A:
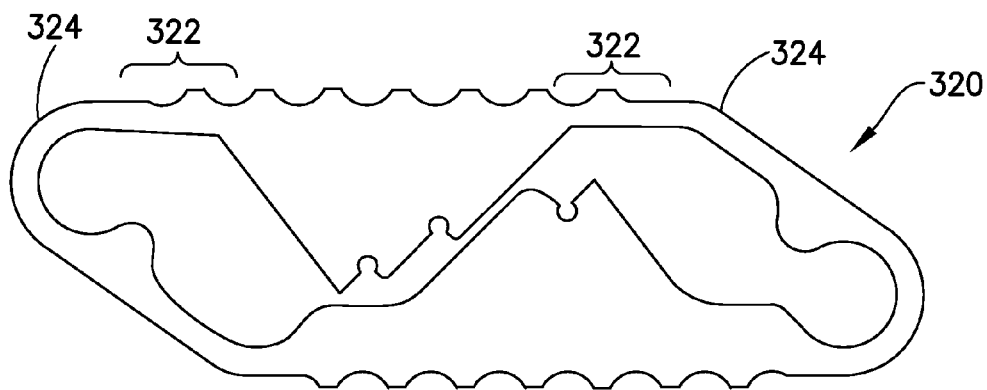
FIGS. 10A, 10B, and 10C show side views of a multi-level variation of the implant, respectively, in collapsed form, partially expanded, and fully expanded form.
Figure 10B:
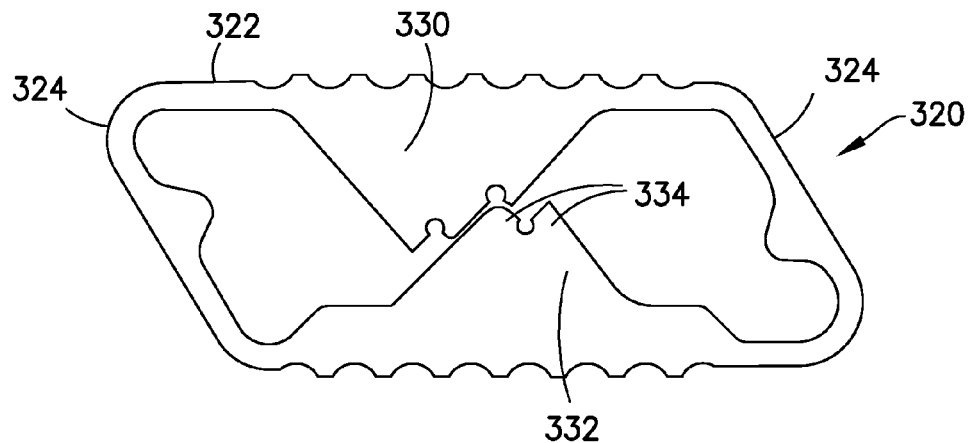
Figure 10C:
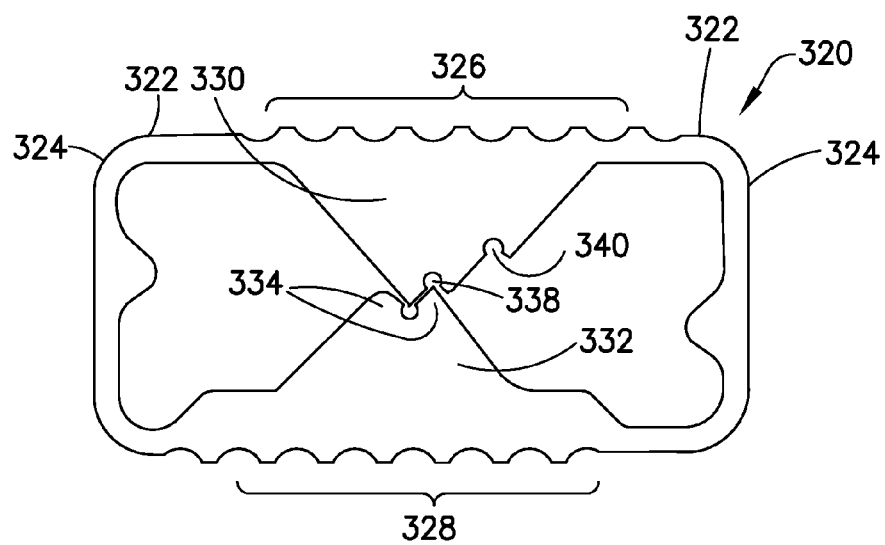

FIGS. 10A-10C show side views of still another variation of my device (320) in which multiple expanded sizes may be selected upon implantation. FIGS. 10A, 10B, and 10C show respectively the collapsed device, the device expanded to a first height, and the device expanded to a second height. Although the implant (320) is facially similar to the device (304) shown in FIG. 9, the deformable regions (322) adjacent the upper deformable joint regions (324) are not substantially stiff in comparison to the upper extended bone contact surface (307) of the FIG. 9 device. If ultimate effect, this variation provides an expanded implant having a smaller upper bone contact surface (326) than its lower bone contact surface (328). These deformable regions (322) permit reformation of the overall structure to various heights in an approximate trapezoidal shape.

This variation of my device (320) also has an upper partial load-bearing column (330) and a lower partial load-bearing column (332). The upper partial load-bearing column (330) includes two latching sites—a lower height site (340) at an intermediate position on the upper partial load-bearing column (330) and a higher height site (338) at the apex of the upper partial load-bearing column (330). The lower partial load-bearing column (332) includes a pair of teeth (334) at its apex forming a portion of an expansion latch. After latching the pair of teeth (334) situated on the lower partial load-bearing column (332) with one or the other of the lower height site (340) or the higher height site (338), the two partial load-bearing columns (330, 332) form a complete load-bearing column at one of the predetermined heights. The deformable regions (332) and the deformable joint regions (324) have been deformed to the shape seen in FIG. 10B or in FIG. 10C.

This device, such as shown in FIG. 9 or 10A-10C may be expanded to specific, unique, predetermined heights by pre-selection of the geometry and placement of the latching sites (or other engagement sites) on the partial load-bearing columns. By "specific" or "discrete" or "unique" or "predetermined," when referring to height, is meant that the device may only be expanded to a height value that is a substantially single value and is stable, i.e., the device is able to support the anatomical load in that position. Instrumentation. The compression of the device using anatomical pressures after expansion will result in less than about 5% of the total expanded height. As discussed with regard to the devices shown in FIGS. 7 and 9, there may be multiple singular, discrete values of the expanded height. Finally, the number of unique, expanded height values for a particular device is equal to the number of pre-configured stability structures, e.g., latching sites or other engagement sites, included in the device.

Kits of any of the implants discussed above where the implants are selected to include a variety of expanded heights, or selected to have the same expanded height and either differing collapsed heights or differing device widths, or selected to include differing angles between the top and bottom bone contact areas, or selected to have a variety of expanded heights with equal differences between the collapsed and expanded states. Each of these kits may further be included with instrumentation to introduce the implants into a chosen site in the human body. Each of these kits may further include written instructions for use.

Figure 11A:
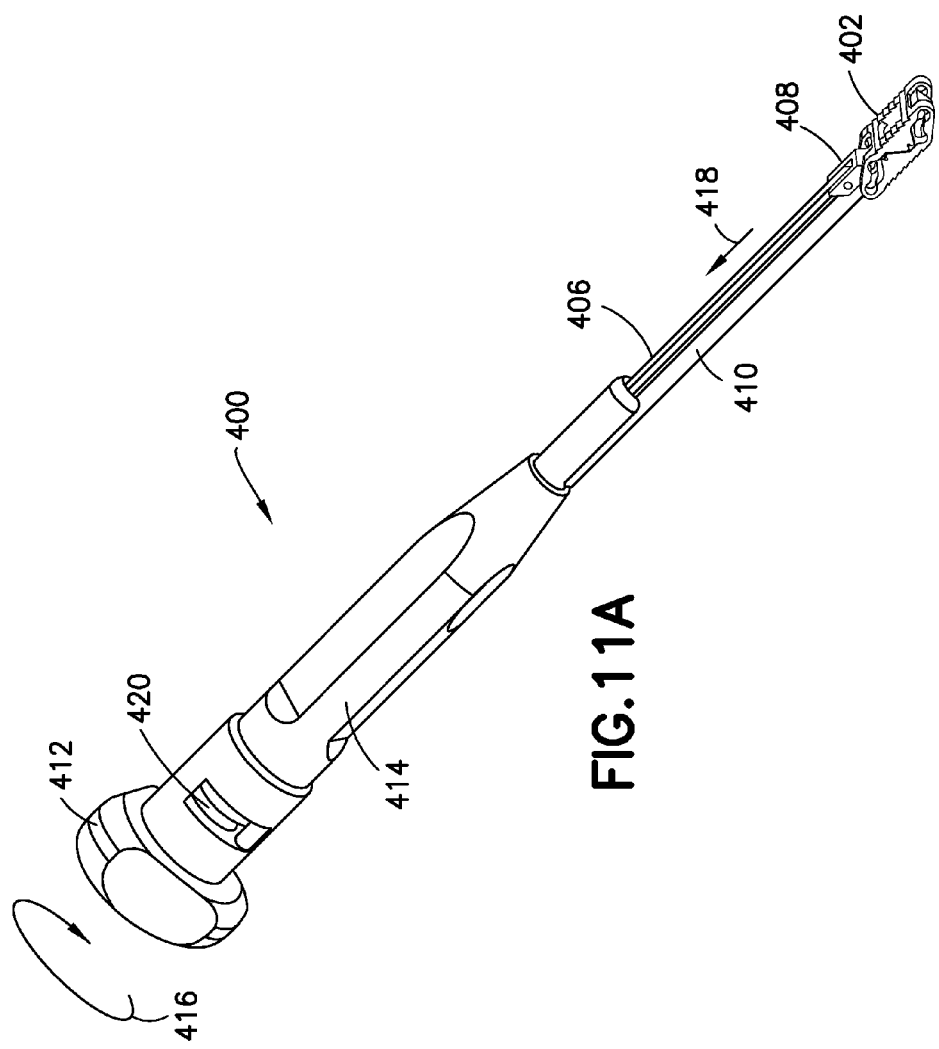
FIGS. 11A and 11B show perspective views of one variation of an implantation tool with, respectively, a collapsed implant and an expanded implant.
Figure 11B:
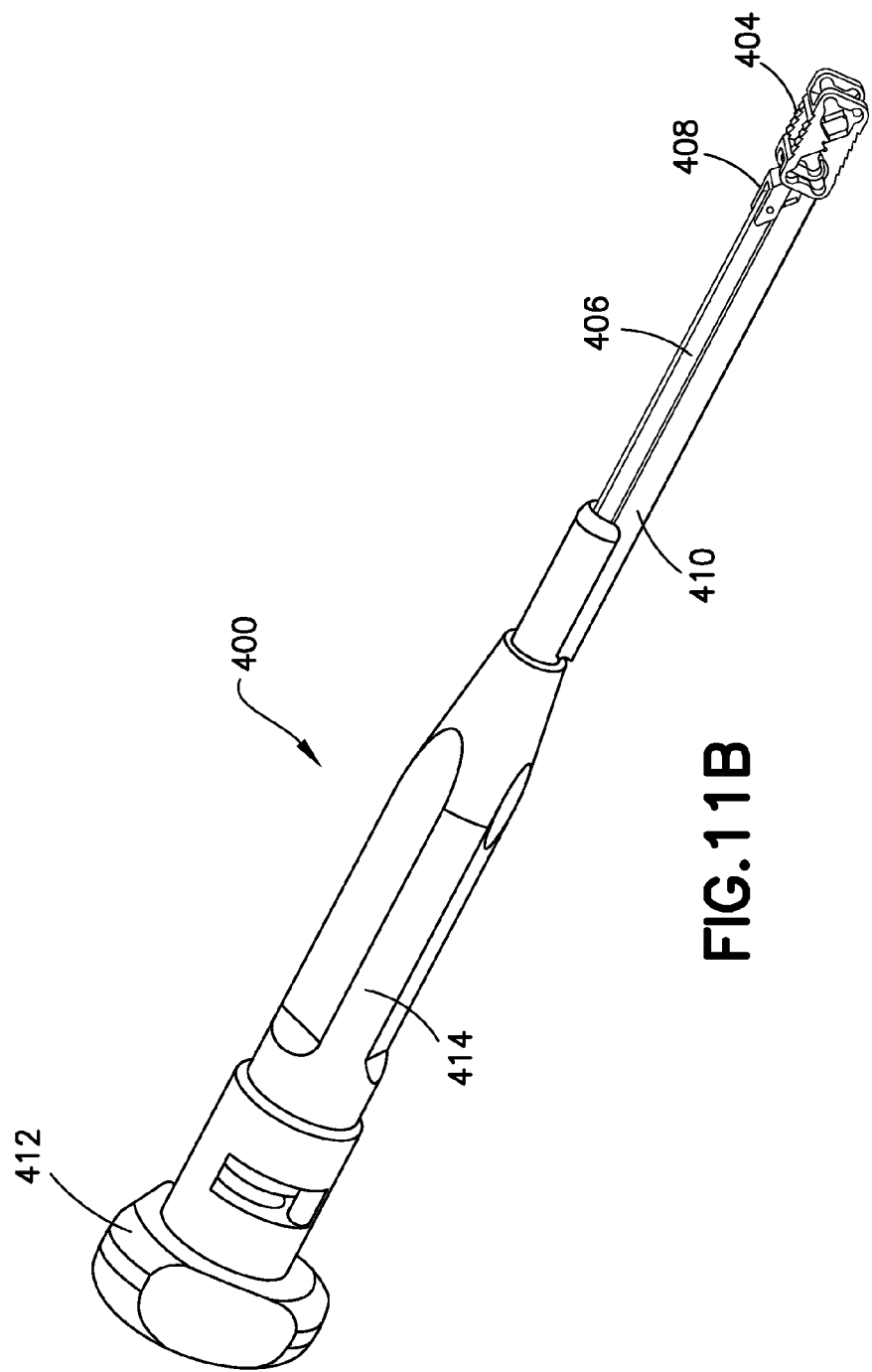

FIG. 11A shows a perspective view of one variation of instrumentation or an implantation tool (400) with a collapsed implant (402) and FIG. 11B shows a perspective view of the implantable tool (400) with an expanded implant (404). The implant (402, 404) in FIGS. 11A and 11B is the variation shown in FIGS. 3A-4C.

As mentioned elsewhere, this variation of the implant (402) is expanded by providing relative motion between one bone contact face of the implant (402) and the other face. The implantation tool (400) accomplishes such push-pull action. As will be discussed in more detail with regard to FIGS. 13A and 13B, the tool (400) incorporates various surfaces that contact surfaces in the implant to pull a distal surface in the implant and to push on a proximal surface (in a generally axial direction) and to actively expand the implant (402).

The implant tool (400) is a straightforward design having a pull rod (406) with a fixture (408) for cooperatively mating with the implant (402) and having a stationary rod (410) that also includes a distal mating fixture (not seen in FIGS. 11A and 11B) that also removably mates with a surface in the implant (402). The implant tool (400) incorporates a twist knob (412) and a stationary grip body (414). A rotary motion (416) applied to the knob (412) applies a linear pulling motion (418) to the pull rod (406). The proximal end of the pull rod (406) may, for instance, be provided with screw threads (not shown) to cooperate with threads associated with the twist knob (412) to provide such linear motion. Included is a ratchet (420) to control the twisting direction of the knob (412) twist and potentially with a lock to maintain the tool (400)/implant configuration (402) in a fixed order prior to use.

This tool (400) provides the desired push-pull motion to expand the implant (404) as shown in FIG. 11B.

Figure 12A:
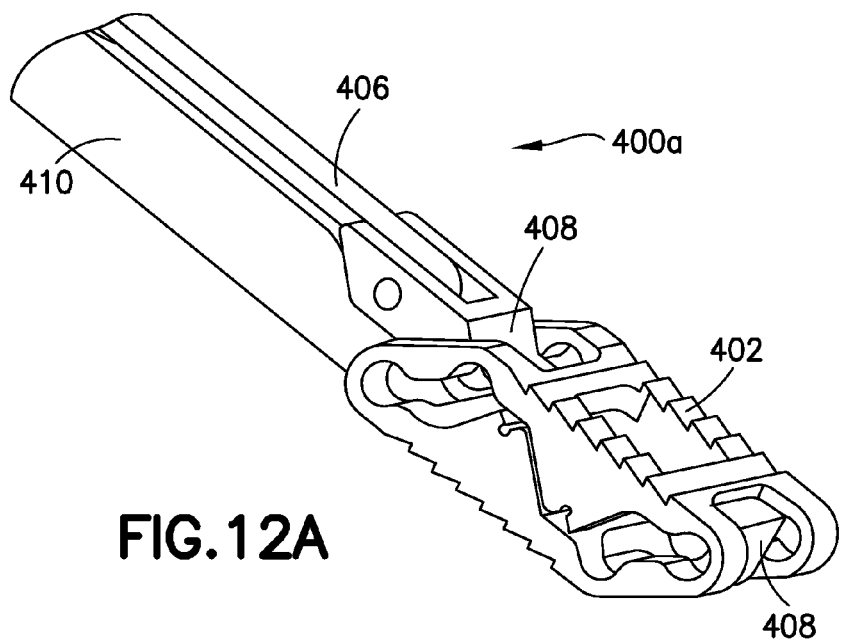
FIGS. 12A and 12B show perspective, close-up views of the distal section of the implantation tool shown in FIGS. 11A and 11B with, respectively, a collapsed implant and an expanded implant.

FIG. 12A shows a close-up, perspective view of the distal tip (400a) of the implantation tool (400) and gives a more detailed view of the pull-rod mating fixture (408) in contact with collapsed implant (402). The pull-rod (406) sits within a channel in the stationary rod (410).

Figure 12B:
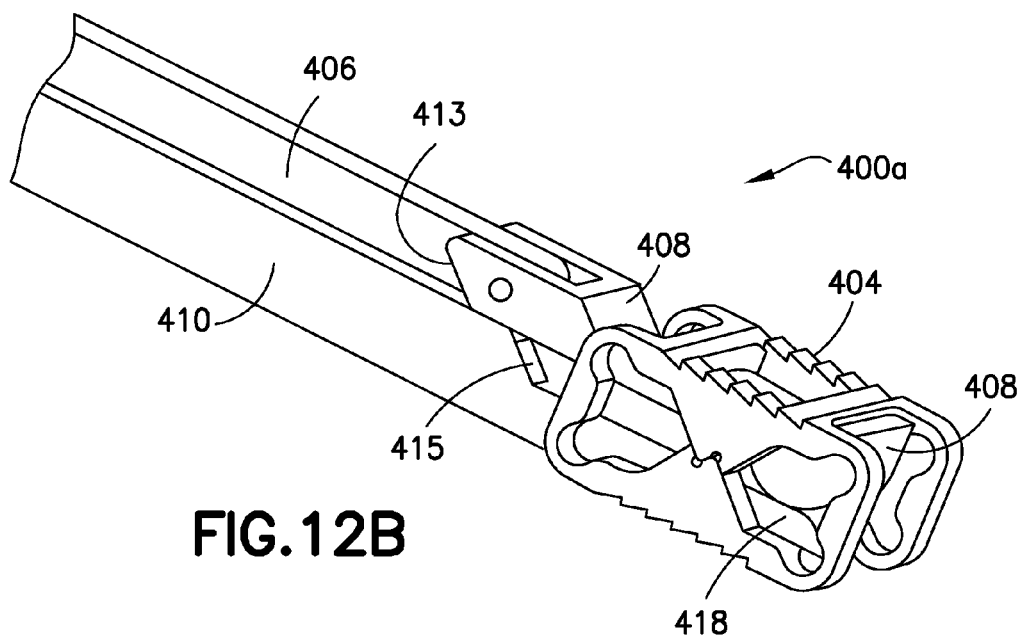

FIG. 12B shows a close-up, perspective view of the distal tip (400a) of the implantation tool (400) with the implant (404) after expansion. In this variation of the implantation tool (400), the pull-rod mating fixture (408) includes an expansion ramp (413). As the pull-rod (406) is pulled proximally, the expansion ramp (413) slides up on a cooperating ramp (415) associated with the stationary rod (410). Similar ramping components are located more distally—moving ramp (416) on pull-rod mating fixture (408) and distal cooperating ramp (418) on stationary rod end (410).

Figure 13A:
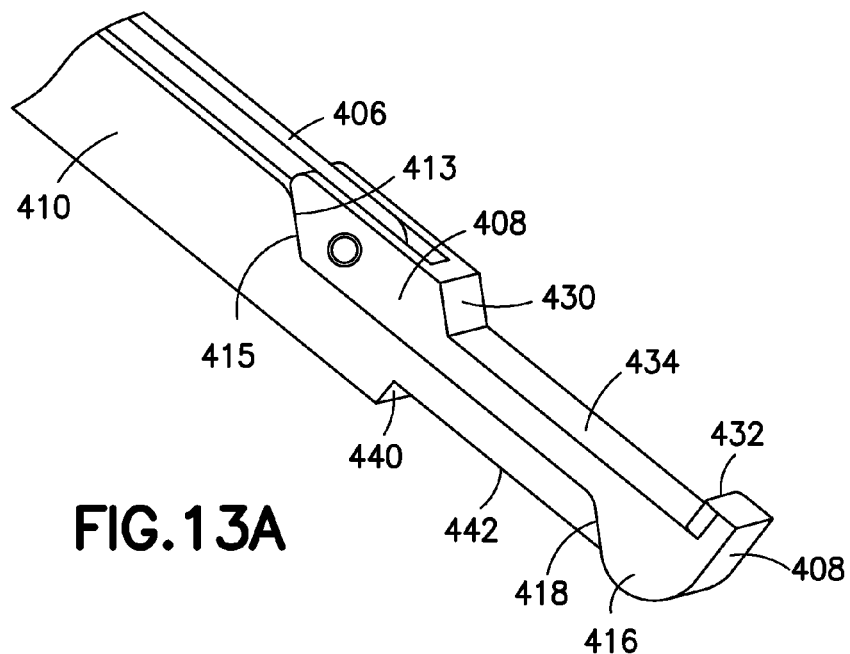
FIGS. 13A and 13B show perspective, close-up views of the distal section of the implantation tool shown in FIGS. 11A and 11B.
Figure 13B:
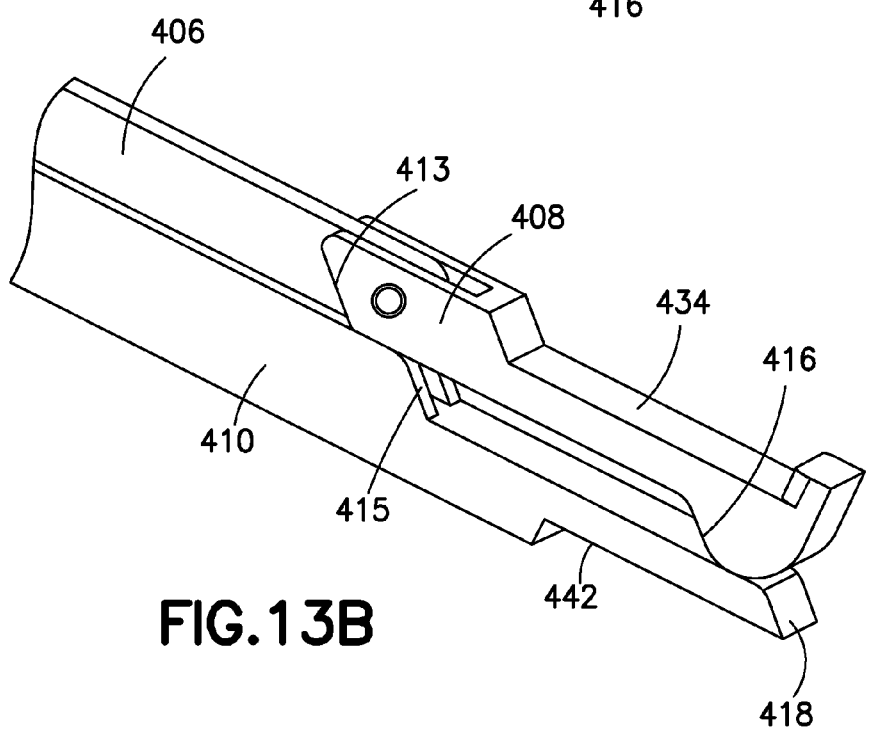

FIGS. 13A and 13B provide close-up, perspective views of the distal end of the implantation tool (400 in FIGS. 11A and 11B) without an implant obscuring details of the tool. FIG. 13A shows the pull-rod (406), the pull-rod mating fixture (408), and the stationary rod (410). This view shows the proximal expansion ramp (413) in contact with the stationary-rod cooperating ramp (415). This view also shows the distally located pull-rod moving ramp (416) in contact with the distal cooperating ramp (418) on the stationary rod (410).

The implant contacts two surfaces of importance on the pull-rod mating fixture (408) during implantation—the distal surface (432) locates and fixes the implant axially in place, the middle surface (434) supports the length of the implant as that side of the implant is pulled proximally during expansion. After expansion is complete, proximal surface (430) disengages the implant and the pull-rod mating fixture (408) as the pull-rod (406) is returned to its starting position and allows removal of the implantation tool (400) from the expanded implant.

Similarly, a stationary surface (440) contacts the implant and maintains it in position, in conjunction with long-wise surface (442) as the opposite side of the implant is pulled proximally and expanded using the pairs of cooperating ramps (413, 415) and (416, 418).

FIG. 13B shows the position of the pull-rod mating fixture (408) after the pull-rod (406) has been pulled proximally to expand the implant. At this final position, the implant is fully expanded and locked at that expanded size by the partial load-bearing columns (120, 122 in FIGS. 1A-1C and 268 in FIGS. 3A-4A). As may be seen in FIG. 13B, the proximal expansion ramp (413) is no longer in contact with stationary rod cooperating ramp (415). The pull-rod moving ramp (416) is no longer in contact with distal cooperating ramp (418). The middle surface (434) on the pull-rod mating fixture (408) has moved away from surface (442) evidencing expansion of the implant.

When used as a fusion device for the spine, the device may be implanted using any of a variety of approaches—anterior, posterior, lateral, etc. Because of the device's initial low profile, the device offers advantages in lower risk transforaminal procedures, e.g., TLIF procedures, or posterior procedures, e.g., PLIF procedures.

Moreover, the device may be expanded at the final placement site or expanded nearby the final placement site and then moved there. The implant may be used to distract vertebrae, to properly align vertebrae, or simply to maintain intervertebral spacing. The devices may be expanded in a direction along the axis of the spine or expanded laterally in an intervertebral space.

Biocompatible Materials

The device may comprise a suitable metallic or polymeric material.

Suitable biocompatible metallic materials include pure titanium, tantalum, cobalt-chromium alloys, titanium alloys (e.g., nickel titanium alloys and tungsten titanium alloys), and stainless steel alloys. Suitable polymeric materials include members of the polyaryletherketone (PAEK) family, e.g., polyetheretherketone (PEEK), carbon-reinforced PEEK, polyetherketoneketone (PEKK); polysulfone; polyetherimide; polyimide; ultra-high molecular weight polyethylene (UHMWPE); or cross-linked UHMWPE. Ceramic materials such as aluminum oxide or alumina, zirconium oxide or zirconia, compact of particulate diamond, or pyrolytic carbon may be included in such polymers.

Osteogenic Compositions

All or a portion of the interior or periphery of the implant may be filled with a suitable osteogenic material or therapeutic composition generally after implantation. Osteogenic materials include synthetic or natural autograft, allograft, xenograft, demineralized bone, bone paste, bone chips, bone strips, structural bone grafts, hydroxyapatite, and calcium phosphate; synthetic and natural bone graft substitutes, such as bioceramics and polymers; other tissue materials including hard tissues, connective tissues, demineralized bone matrix and combinations, and osteoinductive factors. Other bone growth promoting substances may comprise platelet derived growth factors, bone marrow aspirate, stem cells, bone growth proteins, bone growth peptides, bone attachment proteins, bone attachment peptides, hydroxyapatite, calcium phosphate, statins, and other suitable bone growth promoting substances.

Osteogenic compositions may include an effective amount of a bone morphogenetic protein (BMP), $TGF_{\beta 1}$, insulin-like growth factor, platelet-derived growth factor, fibroblast growth factor, LIM mineralization protein (LMP), bone marrow aspirate, stem cells, bone growth proteins, bone growth peptides, and combinations thereof or other therapeutic or infection resistant agents, separately or held within a suitable carrier material.

These materials may be mixed with resorbable materials such as polylactide polymers, polyglycolide polymers, tyrosine-derived polycarbonate polymers, polyanhydride polymers, polyorthoester polymers, polyphosphazenes, calcium phosphate, hydroxyapatite, bioactive glass, PLLA, PLDA, and combinations.

Methods of Use

As noted elsewhere, the implants may be introduced to a treatment site using a number of different approaches—anterior, posterior, lateral, posterior-lateral, etc. Because of the low profile upon insertion, the implant is especially useful in lateral and posterior approaches, e.g., PLIF and TLIF approaches.

Figure 14:
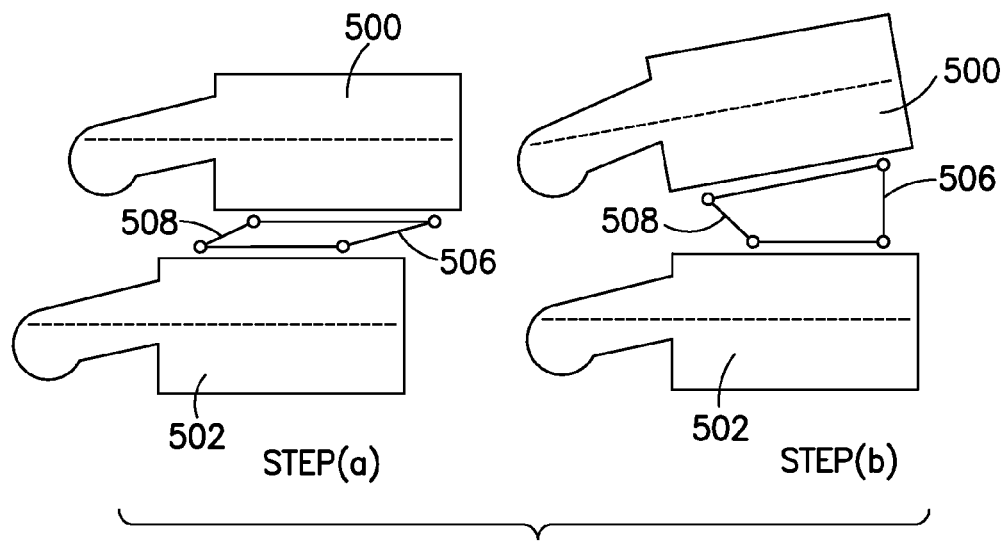
FIGS. 14-17 show examples of implantation procedures for the implant.

FIG. 14 shows the implantation of a variation of the implant into a site having both a collapsed disc and spondylolisthesis (i.e., a condition where a vertebra is displaced anteriorly in relation to the vertebra below). FIG. 14 is a lateral view of an upper vertebra (500) and a lower vertebra (502) separated by an implant (504) having a distal locator arm (506) that is longer than the proximal locator arm (508). Step (a) in the FIG. 14 shows the site having both a collapsed disc and spondylolisthesis with the properly placed, but unexpanded, implant (504). In step (b), the implant (504) has been expanded. Expansion of the noted variation of the depicted implant (504) causes distraction of the vertebrae (500, 502), posterior displacement of the upper vertebra (502), and the restoration of a normal lordotic angle.

Figure 15:
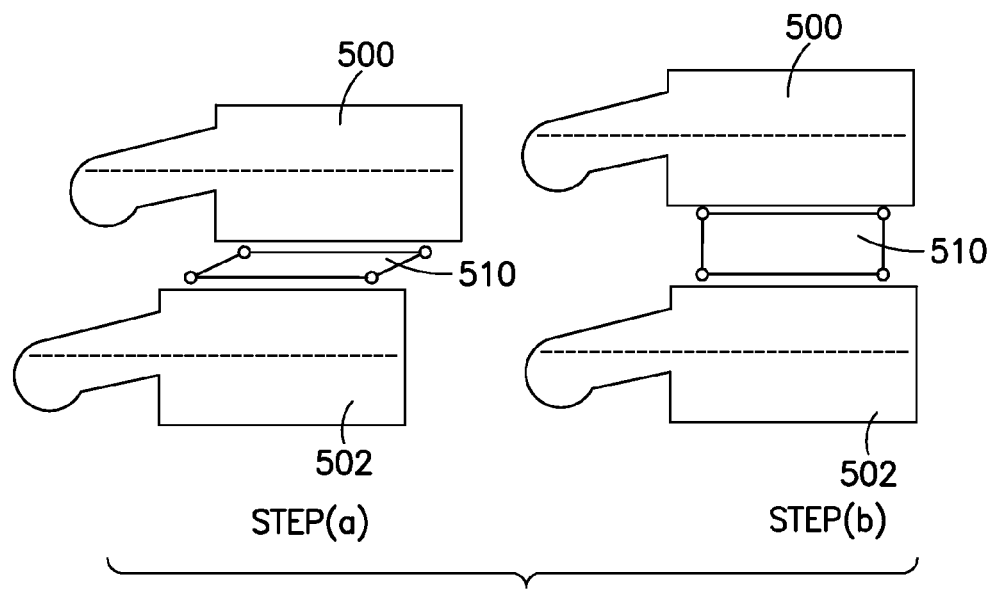

FIG. 15, step (a), shows a lateral view of an intervertebral site between an upper vertebra (500) and a lower vertebra (502) that requires only height preservation.

Step (a) shows the collapsed implant (510) properly situated for implantation. In step (b), the implant (510) has been expanded to contact the surfaces of the vertebral bones. However, the vertebrae (500, 502) have not been distracted nor translated.

Figure 16:
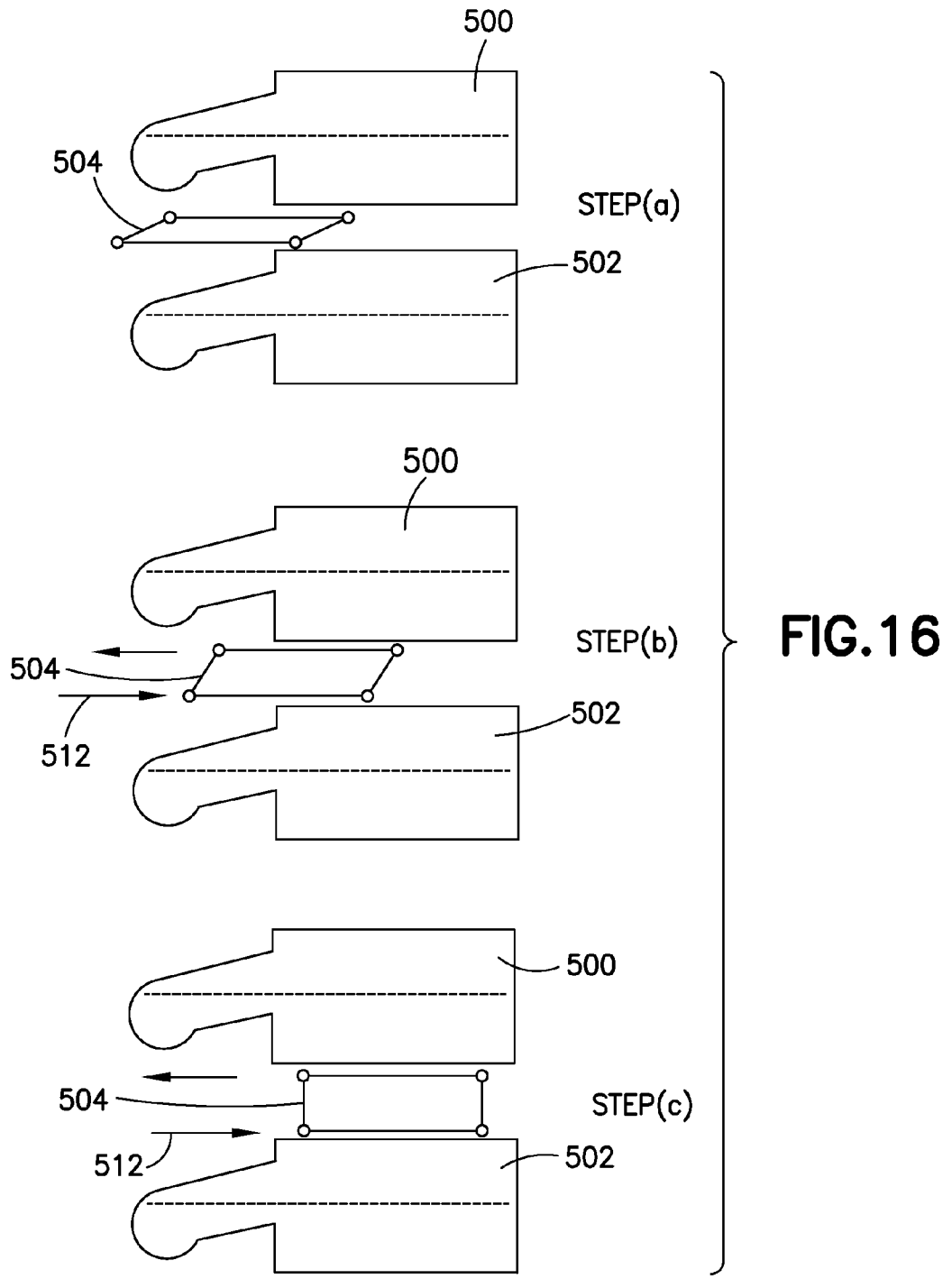

FIG. 16 provides a procedure for inserting an implant into an intervertebral space that requires distraction due to a collapsed disc, but without spondylolisthesis. In step (a), an implant (504) of the type discussed with regard to FIG. 14—having a distal locator arm (506) that is longer than the proximal locator arm (508)—is introduced into the intervertebral space and expanded sufficiently to allow contact with the vertebrae (500, 502). In step (b), the implant (504) is gradually expanded, distracting the vertebrae (500, 502), while being inserted (arrow at 512) into the intervertebral space. In step (c), the implant (504) is fully expanded and has been driven (arrow at 512) into the intervertebral space creating a lordotic angle between vertebrae (500, 502). Using this gradual insertion and expansion procedure, the implant (504) is inserted into the intervertebral space only as far as is optimum for the proper distraction of the vertebrae.

Figure 17:
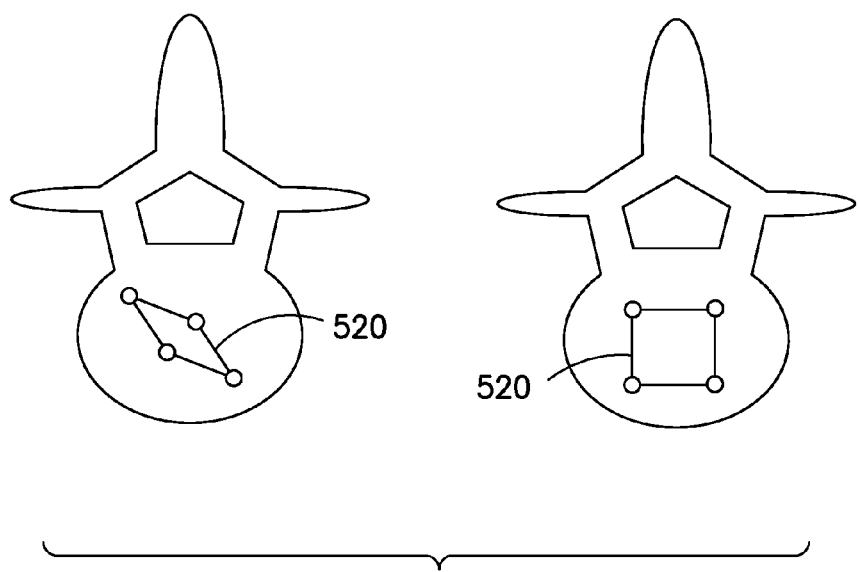

FIG. 17, step (a), shows a top view of a disc space into which an implant (520) has been laterally introduced. Unlike the other variations discussed here, this implant (520) is used only as a spacer. In step (b), the implant has been expanded.

Other Variations

This device may be used other than as an implant. For instance, by constructing the device from an elastic material, the device may be used to measure the size of an interosseous volume. For instance, the instrumentation shown in FIGS. 11A-11B (perhaps with indicia of the push-pull distance traversed by the pull-rod (406 in FIGS. 13A and 13B) during expansion of the device.

Additionally, where particularly specified, one or more of the deformation joints may be substituted with a classical multi-part hinge. One or more deformable regions may remain. Utilizing two or more classical hinges requires that the device not be monolithic.

It is to be understood that all spatial references, such as "horizontal," "vertical," "top," "upper," "lower," "bottom," "left," and "right," are for illustrative purposes only, typically to provide relative positions, and may be varied within the scope of the disclosure.

Other modifications of the present disclosure would be apparent to one skilled in the art. All such modifications and alternatives are intended to be included within the scope of this disclosure as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure.

I claim as my invention:

1. An orthopedic stabilizing device for placement in an interosseous space defined by adjacent bony surfaces, comprising a plastically deformable monolithic body
   a.) expandable along a height axis between a first smaller height to a second larger expanded height by plastic deformation of the monolithic body said monolithic body having an upper bone contact structure and a lower bone contact structure,
   b.) having first and second matchable, partial columns that are not engaged with each other at the first height and are operative to directly engage each other and jointly span the distance between said upper bone contact structure and said lower bone contact structure at the second height to form a supporting structure along the height axis,
   c.) having a longitudinal axis,
   d.) having a lateral axis, and
   e.) operative to contact those adjacent bony surfaces when expanded,
   wherein the first and second matchable, partial columns are latchable directly with each other at the second height.

2. The device of claim 1 wherein the size of the monolithic body is selected to distract the adjacent bony surfaces when expanded.

3. The device of claim 1 wherein the size of the monolithic body is selected not to distract the adjacent bony surfaces when expanded.

4. The device of claim 1 wherein the monolithic body includes an opening along the longitudinal axis when expanded.

5. The device of claim 1 wherein the monolithic body is selectively deformable along the longitudinal axis.

6. The device of claim 1 wherein the monolithic body is selectively deformable only along the longitudinal axis.

7. The device of claim 1 wherein each of the upper bone contact structure and the lower bone contact structure of the monolithic body comprises a bone contact region operative to contact an adjacent bony surface when the monolithic body is expanded.

8. The device of claim 7 wherein the bone contact regions are substantially parallel when the monolithic body is expanded.

9. The device of claim 7 wherein the bone contact regions are not substantially parallel when the monolithic body is expanded.

10. The device of claim 7 wherein the first and second matchable, partial columns are latchable with each other at the second height to maintain the relative position between the bone contact regions when the monolithic body is expanded.

11. The device of claim 7 wherein the first and second matchable, partial columns are latchable with each other at the second height to maintain the relative distance between the bone contact regions when the monolithic body is expanded.

12. The device of claim 7 wherein the first and second matchable, partial columns are latchable with each other at the second height to maintain the monolithic body at the expanded height when the monolithic body is expanded.

13. The device of claim 7 wherein the bone contact regions each comprise more than one segment.

14. The device of claim 1 wherein the first and second matchable, partial columns are latchable with each other at the second height to limit the deformation of the monolithic body to the expanded height when the monolithic body is expanded.

15. The device of claim 1 wherein the first and second matchable, partial columns are operative to maintain the monolithic body at the expanded height by contact between matchable, partial columns.

16. The device of claim 1 wherein the first and second matchable, partial columns are operative to limit the deformation of the monolithic body to the expanded height when the monolithic body is expanded.

17. The device of claim 1 wherein the deformable monolithic body comprises a metal or alloy.

18. The device of claim 1 wherein the deformable monolithic body comprises titanium.

19. The device of claim 1 wherein the deformable monolithic body comprises stainless steel.

20. The device of claim 1 wherein the deformable monolithic body comprises at least one polymer.

21. The device of claim 1 wherein the deformable monolithic body comprises PEEK.

22. The device of claim 1 wherein the deformable monolithic body comprises a metal-polymer composite.

23. A set of the devices of claim 1 comprising multiple devices wherein the difference between the first and second height is of equal value for each such device and the second height for each such device is different from each other device in the set.

24. A set of the devices of claim 1 comprising multiple devices wherein the second height for each such device is the same as each other device in the set and the difference between the first and second height for each such device is different from each other device in the set.

25. An orthopedic stabilizing device for placement in an interosseous space defined by adjacent bony surfaces, comprising a plastically deformable monolithic body
   a.) expandable along a height axis between a first smaller height to a second larger expanded height by plastic deformation of the monolithic body said monolithic body having an upper bone contact structure and a lower bone contact structure, and
   b.) having first and second matchable, partial columns that are not engaged with each other at the first height, that are latchable to each other, and are operative to latch to each other and jointly span the distance between said upper bone contact structure and said lower bone contact structure only at the second height to form a supporting structure along the height axis.

26. An orthopedic stabilizing device for placement in an interosseous space defined by adjacent bony surfaces, comprising a plastically deformable monolithic body
   a.) expandable along a height axis between a first smaller height to a second larger expanded height by plastic deformation of the monolithic body, said monolithic body having an upper bone contact structure and a lower bone contact structure,
   b.) having first and second matchable, partial columns that are not engaged with each other at the first height and are operative to directly engage each other and jointly span the distance between said upper bone contact structure and said lower bone contact structure at the second height to form a supporting structure along the height axis,
   c.) having a longitudinal axis,
   d.) having a lateral axis, and
   e.) operative to contact those adjacent bony surfaces when expanded,
   wherein the first and second matchable, partial columns are operative to maintain the monolithic body at the expanded height by direct contact between the matchable, partial columns.

27. An orthopedic stabilizing device for placement in an interosseous space defined by adjacent bony surfaces, comprising:
   a plastically deformable monolithic body having a distal end and a proximal end, an upper bone contact structure and a lower bone contact structure, a rotatable locator arm adjacent the distal end and a rotatable locator arm adjacent the proximal end, each locator arm being joined to a respective upper bone contact structure and a lower bone contact structure by a deformation joint, a first partial column between said locator arms and projecting from said upper bone contact structure toward said lower bone contact structure, and a second matchable partial column between said locator arms projecting from said lower bone contact structure toward said upper bone contact structure, said body being expandable along a height axis between a first smaller height to a second larger expanded height by the rotation about and plastic deformation of said deformation joints, said first and second matchable partial columns not being engaged with each other at the first height and operative to directly engage each other at the second height to form a supporting structure along the height axis.

28. The device of claim 27 wherein said locator arms are substantially inflexible.

29. The device of claim 28 wherein said upper bone contact structure and said lower bone contact structure are substantially inflexible.

30. The device of claim 27 wherein each of said first and second matchable, partial columns includes an interlocking latch operative to directly interact with each other at the expanded height to maintain the monolithic body at the expanded height.

31. The device of claim 30 wherein each of said upper bone contact structure and said lower bone contact structure has openings to allow ostoegenic materials to flow into and through said monolithic body between adjacent bone surfaces.

\* \* \* \* \*

UNITED STATES PATENT AND TRADEMARK OFFICE
CERTIFICATE OF CORRECTION

| | | |
|---|---|---|
| PATENT NO. | : 8,641,769 B2 | Page 1 of 1 |
| APPLICATION NO. | : 13/809329 | |
| DATED | : February 4, 2014 | |
| INVENTOR(S) | : Hugues Malandain | |

It is certified that error appears in the above-identified patent and that said Letters Patent is hereby corrected as shown below:

In the Specification

Column 5, line 34, replace "S shown in FIG. 1C" with --As shown in FIG. 1C--.

Column 7, line 50, replace "latch together by intermeshing a two" with --latch together by intermeshing two--.

Signed and Sealed this
Seventh Day of July, 2015

Michelle K. Lee
*Director of the United States Patent and Trademark Office*